(12) United States Patent
Lyons

(10) Patent No.: US 7,050,661 B2
(45) Date of Patent: May 23, 2006

(54) PROCESS TO CREATE ARTIFICIAL NERVES FOR BIOMECHANICAL SYSTEMS USING OPTICAL WAVEGUIDE NETWORK

(75) Inventor: Donald R. Lyons, Yorktown, VA (US)

(73) Assignee: TML Photonics, Inc., Yorktown, VA (US)

( * ) Notice: Subject to any disclaimer, the term of this patent is extended or adjusted under 35 U.S.C. 154(b) by 0 days.

(21) Appl. No.: 10/472,564

(22) PCT Filed: Mar. 27, 2002

(86) PCT No.: PCT/US02/09321

§ 371 (c)(1),
(2), (4) Date: Mar. 29, 2004

(87) PCT Pub. No.: WO02/103421

PCT Pub. Date: Dec. 27, 2002

(65) Prior Publication Data

US 2004/0146235 A1    Jul. 29, 2004

Related U.S. Application Data

(63) Continuation-in-part of application No. 09/812,939, filed on Mar. 27, 2001, now abandoned.

(60) Provisional application No. 60/192,372, filed on Mar. 27, 2000.

(51) Int. Cl.
*G02B 6/00* (2006.01)

(52) U.S. Cl. ............................................. 385/12

(58) Field of Classification Search ............ 385/12–13, 385/37, 10
See application file for complete search history.

(56) References Cited

U.S. PATENT DOCUMENTS

| 5,079,555 A | 1/1992 | Turpin |
| 5,191,458 A | 3/1993 | Lyons et al. |
| 5,552,882 A | 9/1996 | Lyons et al. |

*Primary Examiner*—Javaid H. Nasri
(74) *Attorney, Agent, or Firm*—Millen, White, Zelano & Branigan, P.C.

(57) ABSTRACT

A device for responding to touch discrimination comprises an array of optical fibers distributed over a supporting substrate and a UV holographic processor is connected to the fibers rendering the fibers capable of responding to touch discrimination and location identification. The substrate is an artificial limb having the array of optical fibers thereon that have a density substantially similar to that of the human body. Wavelength comparators are associated with the optical fibers, the wave length comparators providing numerous sensing locations in a single fiber strand as part of a complete fiber optic network for mechanical actuation and sensory feed back.

12 Claims, 7 Drawing Sheets

US 7,050,661 B2

PROCESS TO CREATE ARTIFICIAL NERVES FOR BIOMECHANICAL SYSTEMS USING OPTICAL WAVEGUIDE NETWORK

RELATED PATENT APPLICATION

This application is a continuation-in-part of U.S. Pat. No. 09/812,939 filed on Mar. 27, 2001 now abandoned and claims benefit of priority under 35 U.S.C. §119 to provisional patent application Ser. No. 60/192,372, filed Mar. 27, 2000.

FIELD OF THE INVENTION

The present invention is a process for creating a network of artificial nerves for biomechanical systems. More particularly, the present invention is directed to an artificial nervous system design that employs ultra-fine registration of sensory locations in optical waveguide media using metrological tools that permit either Dense Wavelength Division Multiplexing (DWDM), incorporated in its entirety herein by reference, or Dense Time Division Multiplexing (DTDM) of the return signals corresponding to sensory input.

BACKGROUND OF THE INVENTION

There is a serious medical and psychological need for the restoration of sensation for those who have lost sensation due to injury or other mishaps. This patent addresses architectures and techniques for producing sensors and biomechanical structures that could meet these needs. As one example of its use, upon performing the processes outlined in this patent, one possible resulting device could ultimately allow an individual who has need of a prosthetic device to be outfitted with a unit which will give the sensation of 'touch and feel'. Specifically processed optical waveguides from this invention can be incorporated into prosthetic devices or into other human/animal sub-systems and will function as synthetic nerves. Photo-induced holograms within these waveguides act as sensory mechanisms that give intelligent feedback information to the host via embedded microprocessors for mechanical actuation. In the human body, the central nervous system is organized in a hierarchical arrangement with each level having a certain task in motor functioning. Neurons function in the perceptions of the initial stimulus carrying their chemical messengers along a network to the brainstem, which also forms a pathway that descends into the spinal column, to influence motor movement.

SUMMARY OF THE INVENTION

One aspect of the current invention establishes an interface in the vicinity of the truncated portion of the missing limb using specific sites that are known to be sensitive to external stimuli. Optical signals relating strain levels to 'touch responses' are converted into modulated electrical impulses encoded according to the location of its origination signal and its corresponding signal amplitude. It is assumed that some of these signals will travel the same pathways and that the final decoding will be accomplished by training during the rehabilitation phase of the patient. Thus similar, externally attached, devices may be used for persons not necessarily missing a limb to accomplish other sensory functions and, with the use of biologically compatible waveguide materials, such as certain photopolymers, insertion of internal nerves units will be accomplished.

Hill et at. K. O. Hill, Y. Fujii, D. C. Johnson, and B. S. Kawasaki, "*Photosensitivity in optical fiber waveguides: Application to reflection filter fabrication*", Appl. Phys. Lett., 32 (10), pp. 647–9, 1978. first reported and produced a Bragg reflection grating using a longitudinal launch technique. Following Hill's initial work, D. R. Lyons repeated their results using the 488 nm line of an argon-ion laser and shortly thereafter fabricated the first transverse diffraction gratings. Consequently, he established transverse holographic experimental setups with several UV laser sources using the novel approach of side illumination of the fiber. *D. R. Lyons, Internal Reports, Lawrence Livermore National Laboratory, Livermore, Calif.,* 1986–1990.

This approach demonstrated substantial improvement in the fabrication of Bragg gratings and had several advantages including lower power requirements to produce interference gratings, the ability to create highly wavelength selective modal discriminators, the capability of writing holographic patterns at practically any wavelength above the writing laser wavelength, and the inherent facility to write a large number of gratings into a single fiber. Hill's initial method only permitted a single grating to be written in the fiber at a single wavelength. Later studies have been successful in replicating the fabrication of transverse Bragg gratings and have led to a number of useful applications. *G. Meltz, W. W. Morey, and W. H. Glenn, "Formation of Bragg gratings in optical fibers by a transverse holographic method," Opt. Lett.,* 14 (15), 823, (1989). J. D. Prohaska, B. Chen, M. H. Maher, E. G. Nawy, and W. W. Morey "*Fiber Optic Bragg Grating Strain Sensor in Large Scale Concrete Structures*", SPIE vol. 1798 *Fiber Optic Smart Structures and Skins*, (1992).

The current invention allows the construction of distributed sensing networks, based upon Bragg reflection fiber optic filters in a densely packed, single fiber format for distributed strain measurements. The current invention also incorporates feedback data from a number of strain and temperature sensors that have the advantage of pre-registration of its sensing locations using the techniques devised in U.S. Pat. No. 5,552,882, incorporated herein in its entirety by reference. D. R. Lyons, "*Optical Electronic Multiplexing Reflections Sensor System*," U.S. Pat. No. 5,191,458, (March 1993).

The ability to produce grating patterns and the nonlinear mechanisms describing their formation form the basis for ideas involving the use of the length limited Bragg reflection filters as well as their underlying properties. The fabrication of distributed fiber optic sensors relies upon the photorefractive properties of germanium doped silica fibers. In particular, the wavelength region from 170 to 400 nm possesses strong absorption bands for Ge doped optical fiber. M. Josephine Yuen, "*Ultraviolet Absorption Studies of Germanium Silicate Glasses*", *Appl. Opt.*, 21 (1), 136 (1982). For certain optical configurations these gratings act independently to reflect a predetermined number of wavelengths at preset static amplitudes. The dynamic amplitude and the wavelength of the reflections are proportional to the induced strains and strain locations respectively.

An example readout method of involves the illumination of a reflection filter with an SLD (superluminescent laser diode) light source and detection of the back reflected signals at the Bragg wavelengths, FIG. 4. An improved version of this setup incorporates a tunable laser with wavelength scanning capabilities (also shown in FIG. 4). The spectral characteristics of a transverse holographic grating are derived from coupled mode theory. Forward and reverse traveling wave formulations imply that the reflectivity at the Bragg wavelength is given by R=tanh²ξ where $$\xi = \pi \frac{nL}{\lambda}\left(\frac{\Delta n}{n}\right)\eta(V) \text{ with } \eta \approx 1 - \frac{1}{V^2} \; (V \geq 2.4).$$

η is the fraction of integrated fundamental mode intensity in the core, with typical line widths of 20 to 40 GHz.

In the implementation of the current invention, the diagram of FIG. 3 assumes that a first generation 'intelligent arm' will only address sensations from its exterior. However, this technology or some valiant of it will ultimately be used to address interior portions with possible direct interfaces with living tissue through the use of more inert materials.

In view of the aforementioned purposes of the present invention, a metrological standard (referred to in U.S. Pat. No. 5,552,882 referenced above) for fiber Bragg gratings sensors, based upon well-established wavemeter concepts, allows the a priori and accurate determination of nerve center locations and their corresponding response wavelengths. One configuration of such a tool is shown in FIG. 1.

In accordance to the operational principles outlined in U.S. Pat. No. 5,552,882 as well as its reduction to practice detailed in reference. K. R. Samuel, D. R. Lyons, and G. Y. Yan, "*The Realization of a Bragg Reflection Filter Wavemeter*", *Appl. Opt.*, 39 (31), 5755–5761 (2000), laser light from a first laser light source is passed through a beam splitter to create two movable divergent first laser light beams that are reflected from a pair of mirrors so as to converge at a selected interference region common with that of the second set of stationary laser light beams generated in a manner similar to that of the first laser light beams and common with that of all subsequent first laser light beams generated accordingly in similar manner. The associated UV patterns of the first laser light beams are used, upon initial calibration, to write interference patterns into a receptor optical fiber after being compared to the reference patterns derived from a second laser light beams for Bragg wavelength determination. The associated UV patterns of the first laser light beams is used to write interference patterns into a receptor optical fiber after being compared to the reference patterns of the second laser light beams for a priori Bragg wavelength determination. Furthermore, in accordance with detailed aspects of referenced U.S. Pat. No. 5,552,882, the receptor optical fiber of the Bragg reflection filter is an optical waveguide in the form of an optical fiber but ill other aspects of referenced U.S. Pat. No. 5,552,882, the optical waveguide could have other physical configurations and shapes and be made of various optical materials.

The present invention exploits this metrological device by using it or similar devices to create thousands of nerve units similar to the three shown in the bottom circle of the FIG. 2. These individual sensors are capable of transferring information concerning strain ('touch sensation'), temperature ('heat sensation'), and other possible field related phenomena to a microprocessor unit (also depicted in the first diagram). The microprocessor unit, in turn, relays this same information via encoded electrical signals to biological nerve sites. These signal are then interpreted by the brain in a fashion similar to normal sensory inputs that are processed through learned interpretations and correspondingly learned responses.

In consideration of the present invention, this patent outlines a process for the restoration of sensations with 'intelligent biomechanics' using an existing metrological system for spatially registering UV induced sensing points at locations $L_1, L_1, L_1, \ldots$ with corresponding wavelengths $\lambda_1, \lambda_2, \lambda_3, \ldots$ that function as nerve points in optical fibers (see FIGS. 2 and 3).

BRIEF DESCRIPTION OF THE DRAWINGS

Various features and attendant advantages of the present invention will be more fully appreciated and realized as the same becomes better understood when considered in combination with the accompanying drawings, in which referenced characters designate the same or similar parts throughout the several views, and wherein.

DETAILED DESCRIPTION OF THE DRAWINGS

Figure 1:
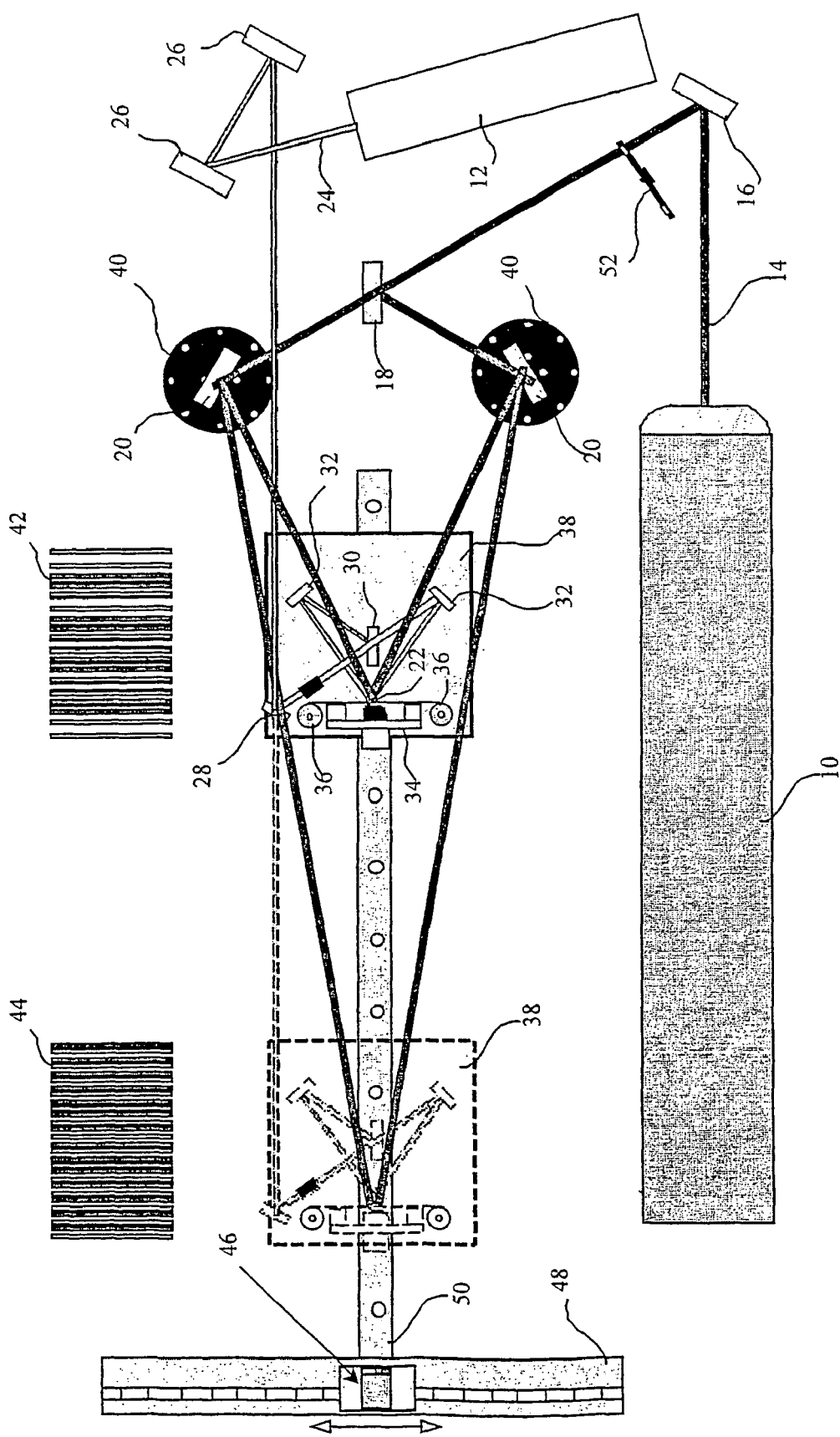
FIG. 1 is a diagrammatic illustration configured in accordance with the principles of the present invention for creating dense wavelength division multiplexed nerve centers in optical fibers.

Referring now to FIG. 1, there is shown a Bragg reflection filter wavemeter 48, configured in accordance with the principles outlined in U.S. Pat. No. 5,552,882 and reduced to practice according to Reference. K. R. Samuel, D. R. Lyons, and G. Y. Yan, "*The Realization of a Bragg Reflection Filter Wavemeter*", *Appl. Opt.*, 39 (31), 5755–5761 (2000), for writing multiple, pre-registered Bragg filters in single fiber units. In its operation, a first ultraviolet (UV) laser 10, generates a coherent first laser beam 14, that reflects from an angled reflector 16, that directs the first laser beam onto a 50% beam splitter 18. The first laser beam 14, is then made to diverge onto two 100% rotating mirrors 20, resident on two, possibly but not necessarily, computer controlled rotating mirror mounts 40. The divergent first laser beams 14, are then made to converge at the same intersection region in space 22, coincident with both a second Reference, stationary set of laser beams 24, generated by the second laser 12.

This arrangement forms a UV interferometer, consisting of components 10, 16, 18, and 20 for directing an interference pattern created by the interference of the first laser light beams from the single laser light source 10, into a common region defined by the image plane of the imaging optics 34 and a second Reference interferometer, consisting of components 26, 28, 30, and 32 for directing an interference pattern created by the second, Reference, laser 12. The first interference pattern can be systematically changed, as illustrated in 42 and 44, by altering the intersection angles of the laser light forming the first laser light beams while keeping their intersection point in the image plane 22. Maintenance of the intersection point is accomplished by a corresponding translation of the stage containing the imaging optics 38, along a linear rail 50, so as to establish a constant intersection point for the first laser light beams 14. The holographic state of each of the subsequent first laser light beams 14, is uniquely defined by the constant state of the second laser light beam 24, which gives rise to the generation a stationary holographic pattern that is subsequently used as a Bragg wavelength marker. These patterns 42 and 44, are then employed in total fringe count ratios using an oscillating dual linear photodiode array 46, to generate electronic counts, corresponding to the frequencies associated with the UV and Reference interference fringes, in conjunction with the calibration constant, allowing the accurate prediction of resulting Bragg wavelength is created by the first laser beams 14. Alternately, these patterns Fourier transform rations can be used in like manner. According as to whether the interference patterns formed by the first laser beam possess low intensity in comparison to that of the second, Reference, patterns, the insertion of an optical modulator 52, for phase sensitive detection and lock-in amplification, is employed.

Figure 2:
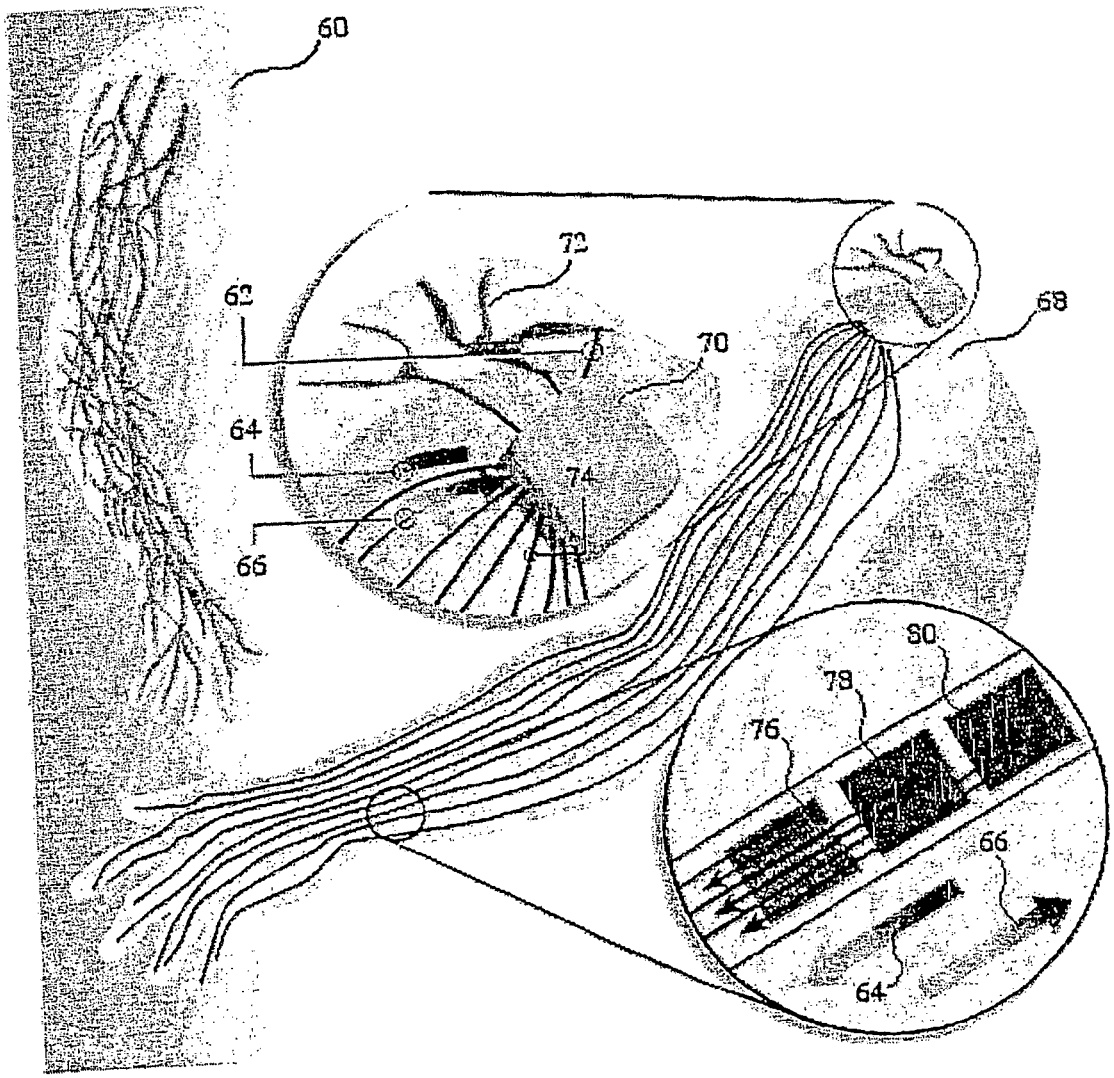
FIG. 2 is an artist conceptual view of the architectural layout of an intelligent artificial arms as described in the principles of the present patent, along with blow up diagrams highlighting several details.

Referring now to FIG. 2, there is shown a diagram depicting a human arm, 60, with its corresponding human nerve network, and an artificial arm 68, with an artificial nerve network containing typical optical components 74, consisting of preprocessed optical fiber waveguides. In accordance with the present patent, and in the event of a catastrophic occurrence, the artificial arm being composed of a network of preprocesses optical fibers 74, allowing transmitted 64, and reflected 66, light pulses carrying sensory information, can be used as a replacement of a missing or irrevocably damaged limb (an arm in the present example). In its implementation, the present invention consists of individual optical fibers 74, of various compositions including but not confirmed to Ge-doped fused silica waveguides and of various geometries including but not confined to the ones shown in FIG. 8, possessing multiple hundreds to thousands of holographic nerve centers 76, 78, 80, etc., shown in the circular blowup of a single fiber-segment at the bottom of FIG. 2, all registered to very high stationary-state accuracy, 0.01% to 0.001% error, in a priori center wavelength determination, designated by $\lambda_1, \lambda_2, \lambda_3$, etc., and location registration, 0.5 mm to 0.1 mm, designated by $L_1, L_2, L_3$, etc. In a further detailing of the concept of the present patent, an implantable control box 70, containing a semiconductor laser (preferably but not necessarily tunable) or other portable source (preferably but not necessarily broadband), an optical fiber interface array, an integrated optical detection array or spectral analysis system, and a low voltage electronic multiplexing device for nerve stimulation acts as the heart of the human artificial arm interface. The final interface components consisting of electrodes 62, and human nerves 72, are member-limited and both act as single channel, multi-signal pathways for sensory feed to the brain for final signal interpretation.

Figure 3B:
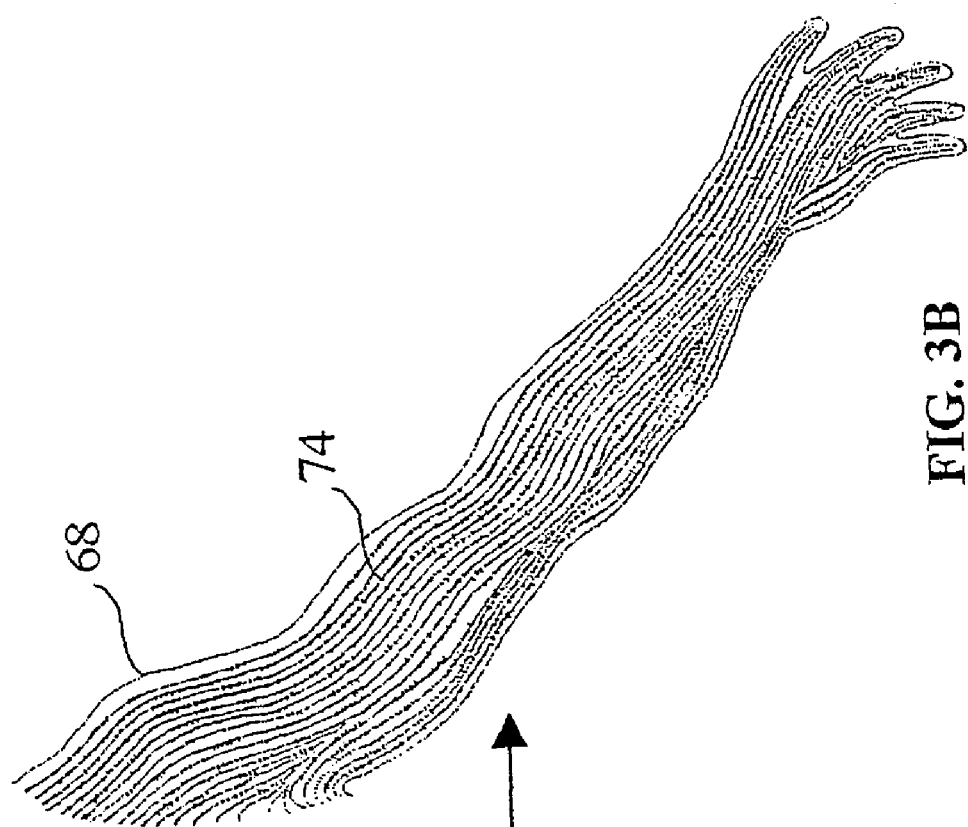
FIG. 3A is a perspective view of the nerve network of a real arm and FIG. 3B is a perspective view of a peripherally configured optical fiber sensor-based artificial arm.
Figure 3A:
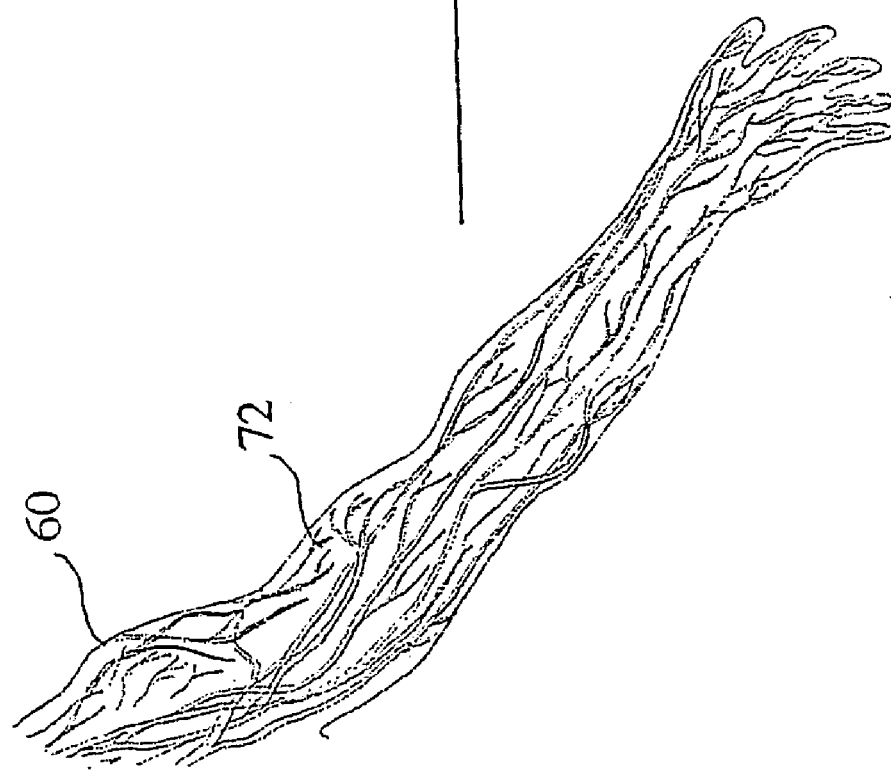

Referring to FIG. 3, we illustrate a general comparison of the human arm 60, and its interior 3-dimensional nerve structures 729 to the artificial arm 68, and its peripherally oriented 2-dimensional fiber optic nerve network 74, planned for the first generation prototypes.

Figure 4:
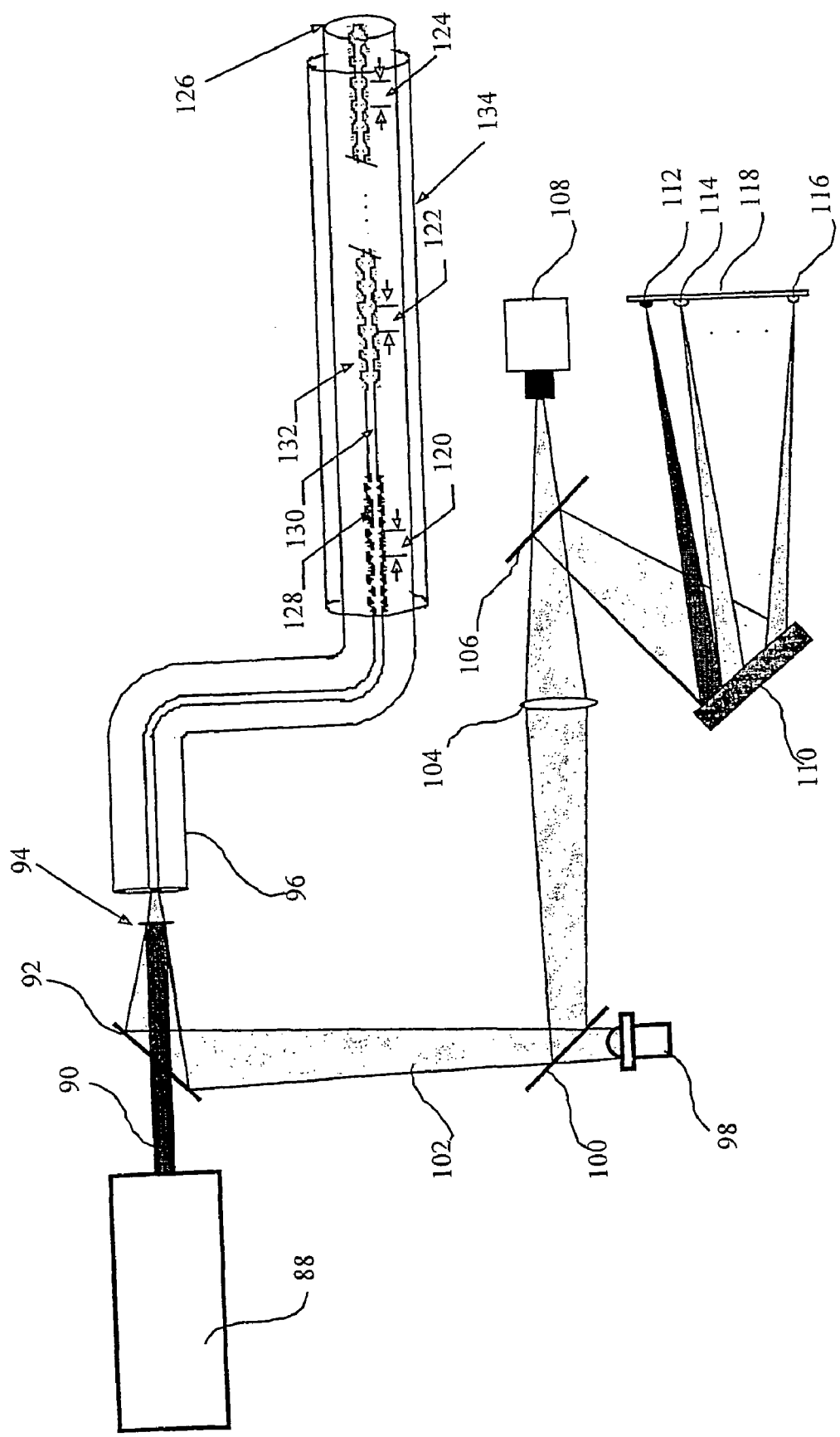
FIG. 4 illustrates the Dense Wavelength Division Multiplexed (DWDM) architecture for a single artificial nerve strand along with various readout schemes configured in accordance with the principles of the present invention.

Referring to FIG. 4, there is shown a typical single mode fiber optic strain and temperature sensor array created by employing UV implanted holographic filters similar to the ones to be-used in the present patent. (See U.S. Pat. No. 5,191,458). In one preferred form of the present invention shown in FIG. 4, light sources 88 or 98, capable of multiple wavelength generation spanning the range of wavelength filters 120, 122, ..., 124, corresponding to Bragg filter resonance wavelength $\lambda_1, \lambda_2, ..., \lambda_n$, illuminate the holographic filters of a preprocessed optical fiber 96, consisting of a cladding region 132, and a guiding core region 130. The light source 88, might consist of a narrow linewidth tunable laser while the alternate light source might consist of a broadband superluminescent laser diode. One or the other of these sources generates an illuminating transmitted beam 90 or 102, that passes through a beam splitter 92 or 100, respectively, that is then focused into the sensing fiber 96, by way of a micro-lens 94. Upon entering the fiber containing holographic index of refraction modulations of given modulation amplitudes 128, and distinct modulation frequencies 120, 122, ..., and 124, within the gliding region 130 of an optical fiber, the portions of the spectrum whose wavelength is corresponding to twice the Bragg filter modulation spacings are back-reflected out of the input end of the fiber. The beam, composed of only those frequencies associated with $\lambda_1, \lambda_2, ..., \lambda_n$, strikes the partial reflectors 92 and/or 100 and enters a focusing lens 104, and passes into a spectrum analyzer 108, or onto a wavelength dispersive element 110, that separates the individual wavelengths $\lambda_1, \lambda_2, ..., \lambda_n$, onto photodiodes 112, 114, ..., 116 located along an electronic array 118. As an additional noise suppression technique, the optical fiber 96, is coated on its end with an absorptive coating 126.

Figure 5:
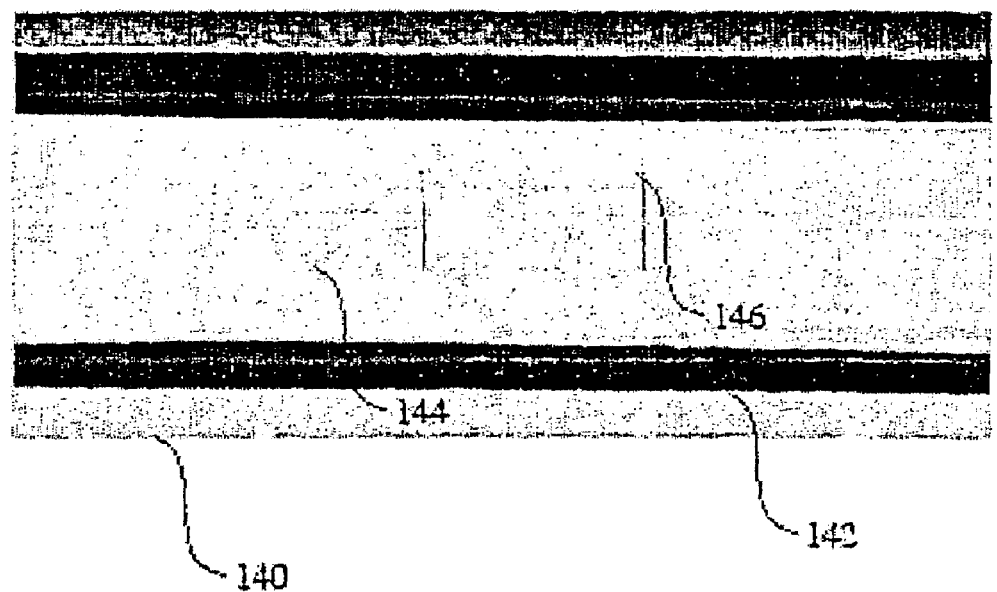
FIG. 5 is a photomicrograph of a portion of an actual single grating (artificial nerve center) with a further magnified small section cutout highlighting the index of refraction modulations (light and dark lines) that form the basis of the physical mechanisms behind the present patent.

Referring to FIG. 5, there is shown a photomicrograph of a superimposed image 140, of the holographic grating pattern 144, with blown up image 146, and an optical fiber image 142, for a wavelength calibration reference.

Figure 6:
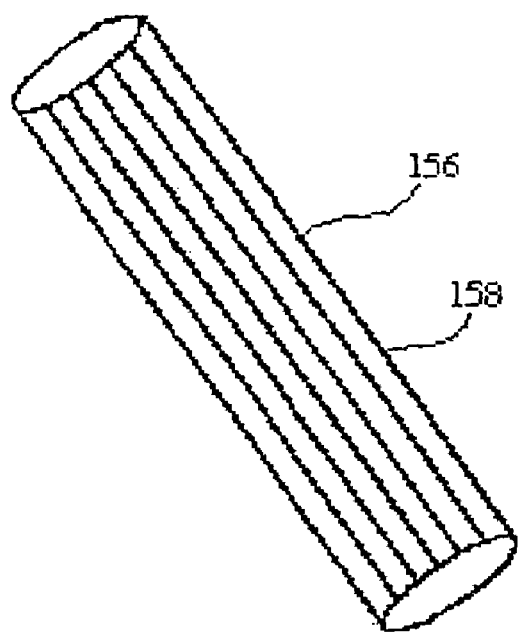
FIG. 6 illustrates one possible layout configuration of the sensor arrays along the outer portions of a structure such as a human arm as described in the present patent.

Referring to FIG. 6, there is illustrated the fiber sensor array 158, shown to be oriented along the longitudinal axis of the artificial limb symbolically displayed as a cylindrical tube 156.

Figure 7:
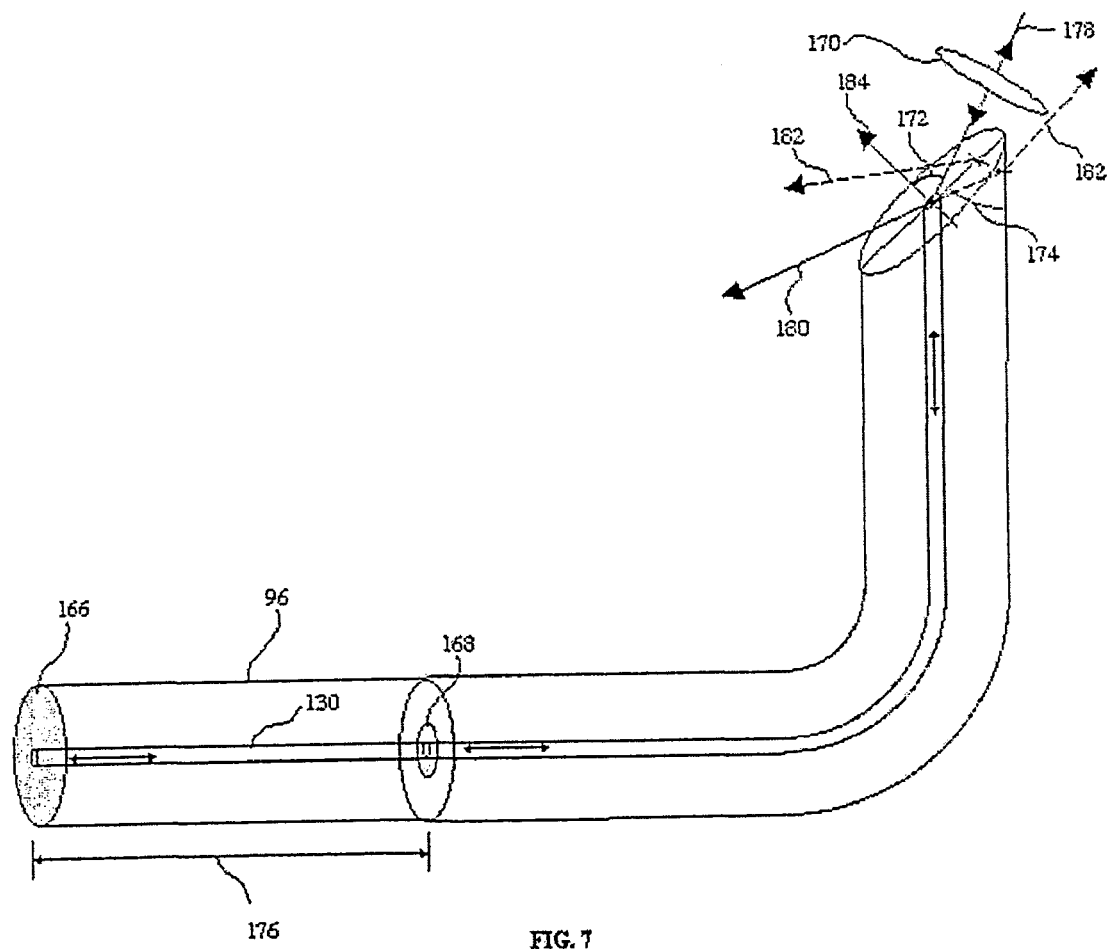
FIG. 7 shows the Brewster angle input fiber technique typically incorporated into all sensor configurations described in the present patent to take advantage of fiber input noise suppression as well as input polarization selection and, FIG. 8 illustrates the three most-likely fiber types that will be used as artificial fiber optic nerves as outlined in the details of the present invention.

Referring to FIG. 7, there is described a typical wedged lead-in fiber 96, creating a Fabry-Perot interferometer, possessing a guiding region 130, a 60% partial gold-coated reflector 168, and a 100% gold-coated end 166 of a given gauge length 176. As in the case of the present invention, the Brewster or near Brewster angled fiber input allows the analysis of weak optical signals by optically suppressing back reflected insertion noise due to the interference of the typically parallel input fiber endface. In addition, the angled nature of the endput end maximizes the light throughput by increasing the interaction cross section of the guiding fiber channel while minimizing the Fresnel reflection associated with the air to glass (or other higher index material) interface. The details of the wedge are as follows: A beam 178, passes through a focusing microlens 170, and splits into several parts, including a (not necessarily) minimal Fresnel reflected beam 80 and a transmitted beam. The back-reflected beams return from the sensor end, without interference with the input, and splits into at least three dominant portions. There is a strong core refracted beam 178, an internally reflected and end face refracted weak beam 182, and a week second refracted beam 182. The two important angles are the incident input angle 172 (defined relative to the normal vector 184), and the wedge angle 174 associated with the fiber.

Figure 8:
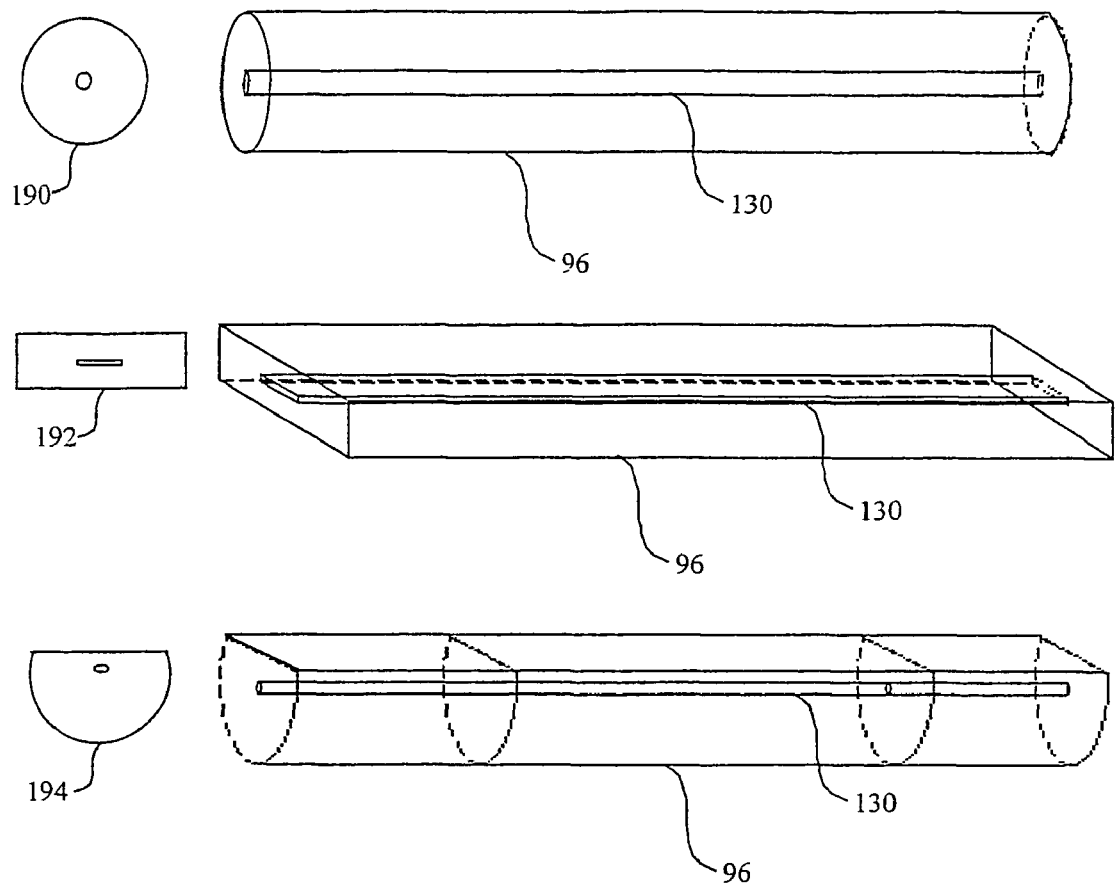

Referring to FIG. 8, there is shown three fiber types that are considered the most probable fiber geometries for use as artificial nerves. Each has a cladding region 96, surrounding a guiding core region 130. The first and most prevalent geometrical shape is the circular one shown at the top of FIG. 8. The most preferred geometry is shouts in the middle figure and consists of a rectangular waveguide which has never been commercially available due to manufacturing and handling issues but would allow easy holographic patterning and more sensitive arrays because of the smaller distances between the perturbing phenomena and the sensing (core) regions of the fibers. An intermediate geometry contained in the D-shaped fiber at the bottom of FIG. 8, allows easy access to the guiding (core) regions of the fiber for greater sensitivity along with a flat, non-planewave distorting face, but also has some of the same handling problems associated with the flat fiber. In addition, this fiber is difficult to obtain and is in very short supply. Thus, for the present invention, the commercially available circular fibers will most likely be used along with sensitivity enhancing mechanisms incorporated as well.

Sensor Fabrication and Evaluation

Bragg sensors are fabricated by exposing the sides of single-mode Ge-doped fibers to concentrated coherent UV radiation. Multiple sensing regions are created in a single fiber by writing distinct interference patterns in sequential steps while translating the fiber between writing sessions. The goal is to produce spatially distinct Bragg regions and allow localized measurement of stress, strain, or temperature along a given region of the fiber. To help perform this exposure and fabricate Bragg sensors with highly accurate wavelength calibration features, a special device called a Bragg Reflection Filter Wavemeter is being developed. *Methods of and Apparatus for Calibrating Precisely Spaced Multiple Transverse Holographic Gratings in Optical Fibers*, U.S. Pat. No. 5,552,882, Sep. 3, 1996, D. R. Lyons; Z. U. Ndlela. This new device essentially establishes a wavelength standard for precise modulation spacing of a Bragg grating and accurately calibrates each writing location against a known laser standard. Each sensor is distributed along the length of the optical fiber in referenced positions, and has high reflectivity whenever the optical wavelength is equal to twice the grating spacing. Since the grating spacing is extremely responsive to external perturbations such as strain and temperature, changes in these parameters cause a change in the reflectivity where these sensors possess typical linewidths of ~0.2 nm.

The photomicrograph shown in FIG. 5 illustrates the principal upon which the wavelength standard is based. The interference pattern shown is the actual writing pattern in the fiber. Its corresponding Bragg resonance is empirically determined to high accuracy with a high-resolution laser probe. A second pattern is then used, upon its calibration, to determine the resonance of all subsequent interference patterns based upon dual fringe counts in a similar far field image. The hardware of the wavelength comparator (or wavelength standard) system, shown in FIG. 1, uses a standard pattern that is produced in the inertial frame of a moving interferometer and a variable writing pattern that is located in the stationary laboratory frame. This patented device or one of similar character, mentioned earlier, allows accurate wavelength markers (sensing regions) to be written in a single fiber at evenly spaced wavelengths locations.

FIG. 6 shows a fiber sensor array along the longitudinal axis of the artificial and of FIGS. 2 and 3B.

Although the signals coming from these sensors are subject to the inherent noise associated with the lead-in fiber reflections, these signals through suitable optical noise suppression can readily be eliminated and thus allow the characterization of perturbing phenomenon. FIG. 7 shows a completed in-line fiber optic Fabry-Perot sensor employing optical noise suppression or near Brewster angle input. The Bragg sensors are fabricated by exposing the sides of single-mode Ge-doped fibers to concentrated, coherent UV radiation. Multiple sensing regions are created in a single fiber by writing distinct interference patterns in sequential steps while translating the fiber between writing sessions. The aim is to produce spatially distinct Bragg regions and allow localized measurement of stress, strain, or temperature along a given region of the fiber. To help perform this exposure and fabricate Bragg sensors with highly accurate wavelength calibration features, a special device called a Bragg Reflection Filter Wavemeter is used. K. O. Hill, Y. Fujii, D. C. Johnson, and B. S. Kawasaki, "*Photosensitivity in optical fiber waveguides: Application to reflection filter fabrication*", Appl. Phys. Lett., 32 (10), pp. 647–9, 1978. This new device essentially establishes a wavelength standard for precise modulation spacing of a Bragg gratings and accurately calibrates each writing location against a known laser standard. Each sensor is distributed along the length of the optical fiber in referenced positions, and has high reflectivity whenever the optical wavelength is equal to twice the grating spacing. Since the grating spacing is extremely responsive to external perturbation such as strain and temperature, changes in these parameters cause a change in the reflectivity. The photomicrograph shown in FIG. 5 illustrates the principal upon which the wavelength standard is based. The interference pattern shown is the actual writing pattern in the fiber. Its corresponding Bragg resonance is empirically determined to high accuracy with a high-resolution laser probe. A second pattern is then used, upon its calibration, to determine the resonance of all subsequent interference patterns based upon dual fringe counts in a similar far field image.

Biological Receptors: the Sensory System

The perception, or understanding of external sensation by neurons occurs by a three step process: 1) transduction caused by a stimulus which creates an action potential; 2) transmission of the data through the nervous system; and 3) interpretation of the data by the brain. Although this three-step process of sensory perception cannot be separated, sensory information is gathered by neural activity. Activity at the neuron is interfaced with the surroundings via sensory receptors. Sensory receptors respond to changes in the external environment and this information concerning the external environment (extrinsic to the cell) can cause a difference in membrane potential. These receptors are either specialized cells at the ends of neurons, or separate cells that influence the physiology of the ends of neurons. These input signals might come in many forms, for example pressure, temperature, light, sound and injury (damage). Regardless of the initial origin of the input signal, the final result is that information from the receptor is linked to the nervous system; thus, the energy that activated the sensory receptor as an external stimulus, leads to a signal transduction process. The transduction process for all receptors involves changes in the chemical potential of ion channels. The channels occur in specialized cells and allow for a change in bulk flow of ions across the receptor membrane. Any change in bulk flow rate can result in, or generate, a change in electrical potential. This happens because a change in ion concentration across the membrane allows for a current to be generated from the receptor membrane to the axon. This current can then proceed to a region where the membrane can create a potential. In cells where the receptor membrane is on a separate cell, the receptor potential causes the release of neurotransmitters that can diffuse across the extra cellular space between the receptor cell and the neuron and bind to specific sites to cause a graded, electrical potential in the neuron. This electrical potential leaves the cells as a signal that can be "fed" into a sensory pathway (a chain of end-to-end neurons). Finally, the sensory pathway provides a mechanism by which to run the signal from the neurons to the central nervous system and eventually to the brain where it is recognized in the cerebral cortex.

The Control of Body Movement

The central nervous system is organized in a hierarchical arrangement with each level having a certain task in motor functioning. Neurons function in the perception of the initial stimulus. They carry their chemical messengers along a network to the brainstem, which also forms a pathway that descends into the spinal column, to influence motor movement. Ultimately, this process can be used to establish an interface at the truncated portion of the missing limb (or other biological sub-system) using specific sites that are known to be sensitive to external stimuli. Optical signals concerning strain levels ('touch responses') can be converted into modulated electrical impulses that are encoded according to location, wavelength response, and/or signal amplitude. Although some of these signals will travel the same pathways, the decoding will be interpreted by training during the rehabilitation or training phase of a subject.

All patents and publications cited herein are incorporated herein by reference in their entirety.

From the foregoing description, one skilled in the art can easily ascertain the essential characteristics of this invention, and without departing from the spirit and scope thereof, can make various changes and modifications of the invention to adapt it to various usages and conditions.

I claim:

1. A device for responding to touch discrimination, comprising
    an array of optical fibers distributed over an artificial limb providing a supporting substrate for an array of optical fibers thereon having a density similar to that of the human body;
    wavelength comparators associated with the optical fibers, the wave length comparators providing numerous sensing locations in a single fiber strand as part of a complete fiber optic network for mechanical actuation and sensory feed back, and
    a UV holographic processor connected to the optical fibers rendering the optical fibers capable of responding to touch discrimination and location identification.

2. The device claim 1 further including a continuous wave scanner and a readout for wavelength multiplexed signals in the optical fibers with UV induced nerve centers.

3. The device claim 1 further including sensors fabricated and incorporated into an artificial skin of a prosthetic device for simulation of a touch sensation allowing the creation of a more fully functional substitute for a lost limb or appendage.

4. The device claim 1 further including a distributed Bragg fiber optic sensor system using specifically processed optical fibers capable of responding to touch discrimination and location identification.

5. The device of claim 1 further including a system for scanning and reading out signals in wavelength multiplexed optical fibers using holographically induced Bragg gratings.

6. The device claim 1 further including encasement schemes for superposition of multi-sensory region fibers onto arms or other intelligent structures, and
    a system having an ability to respond to touch and position discrimination for a finite number of locations by having response through an audible computer interface connected thereto.

7. The devices claim 1 wherein the array of optical fibers are evenly spaced having multiple holographic gratings in single mode fibers.

8. The device of claim 1 further including narrow linewidth lasers as well as spectrum analyzers for characterizing wavelengths, linewidths, and reflective of gratings to characterize an entire sensing network.

9. The device of claim 1 wherein the substrate is an artificial arm and the array of fibers is longitudinally oriented and evenly distributed about the periphery of the artificial arm to create an optical fiber sensory WDM network with peripheral architectures.

10. The device claim 1 further including a scanning laser system, a miniature spectrum analyzer, or a broadband superluminescent source with a miniature diode array for providing a miniaturized optical readout.

11. The device claim 1 wherein the artificial limb is a prostheses with surface bonded or embedded fibers and an additional polymer overlay with the sensitized fibers in the overlay, the prosthesis being covered with a skin-like material.

12. The device claim 1 wherein the substrate is an intelligent structure interfaced with a talking computer to simulate responses of a human host in terms of touch sensitivity and location description.

* * * * *

UNITED STATES PATENT AND TRADEMARK OFFICE
CERTIFICATE OF CORRECTION

PATENT NO. : 7,050,661 B2  
APPLICATION NO. : 10/472564  
DATED : May 23, 2006  
INVENTOR(S) : Donald Lyons It is certified that error appears in the above-identified patent and that said Letters Patent is hereby corrected as shown below:

Column 10, line 6, reads "device claim" should read -- device of claim --  
Column 10, line 9, reads "device claim" should read -- device of claim --  
Column 10, line 14, reads "device claim" should read -- device of claim --  
Column 10, line 21, reads "device claim" should read -- device of claim --  
Column 10, line 28, reads "devices claim" should read -- device of claim --  
Column 10, line 40, reads "device claim" should read -- device of claim --  
Column 10, line 45, reads "device claim" should read -- device of claim --  
Column 10, line 50, reads "device claim" should read -- device of claim --

Signed and Sealed this

Sixth Day of February, 2007

JON W. DUDAS  
*Director of the United States Patent and Trademark Office*